United States Patent [19]

Maszkiewicz et al.

[11] Patent Number: 5,135,510
[45] Date of Patent: Aug. 4, 1992

[54] HYPODERMIC SYRINGE

[76] Inventors: Mark E. Maszkiewicz, 128 Claridge Dr., Coraopolis, Pa. 15108; Mary C. Miller, 1218 Wareman Ave., Pittsburgh, Pa. 15226

[21] Appl. No.: 687,562

[22] Filed: Apr. 19, 1991

[51] Int. Cl.$^5$ ............................................. A61M 5/32
[52] U.S. Cl. ..................................... 604/195; 604/198
[58] Field of Search ............... 604/198, 192, 263, 187, 604/227, 195, 110

[56] References Cited

U.S. PATENT DOCUMENTS

| | | | |
|---|---|---|---|
| 2,847,996 | 8/1958 | Cohen et al. | |
| 3,130,724 | 4/1964 | Higgins et al. | 604/227 |
| 3,306,290 | 2/1967 | Weltman | |
| 4,356,822 | 11/1982 | Winstead-hall | |
| 4,675,005 | 6/1987 | DeLuccia | 604/110 |
| 4,702,738 | 10/1987 | Spencer | 604/198 |
| 4,723,943 | 2/1988 | Spencer | 604/198 |
| 4,725,267 | 2/1988 | Vaillancourt | 604/192 |
| 4,731,059 | 3/1988 | Wanderer et al. | 604/192 |
| 4,735,618 | 4/1988 | Hagen | 604/192 |
| 4,743,233 | 5/1988 | Schneider | 604/192 |
| 4,767,413 | 8/1988 | Haber et al. | 604/198 |
| 4,787,891 | 11/1988 | Levin et al. | 604/136 |
| 4,801,295 | 1/1989 | Spencer | 604/198 |
| 4,804,371 | 2/1989 | Vaillancourt | 604/198 |
| 4,840,619 | 6/1989 | Hughes | 604/187 |
| 4,850,977 | 7/1989 | Bayess | 604/263 X |
| 4,850,994 | 7/1989 | Zerbst et al. | 604/198 |
| 4,871,355 | 10/1989 | Kikkawa | 604/198 |
| 4,894,055 | 1/1990 | Sudnak | 604/198 |
| 4,900,311 | 2/1990 | Stern et al. | 604/198 |
| 4,911,693 | 3/1990 | Paris | 604/192 |
| 4,927,416 | 5/1990 | Tomkiel | 604/198 |
| 4,929,237 | 5/1990 | Medway | 604/198 |
| 4,946,446 | 8/1990 | Vadher | 604/198 |
| 4,961,730 | 10/1990 | Poncy | 604/198 |

Primary Examiner—John D. Yasko
Attorney, Agent, or Firm—Buchanan Ingersoll

[57] ABSTRACT

A device for preventing exposure of a contaminated hypodermic needle to health care personnel is provided. A syringe barrel having a flange at one end and a hypodermic needle at the other end is adapted to receive a plunger. A protective guard fits around the syringe barrel and moves relative thereto. The protective guard can assume different positions in which the hypodermic needle is either exposed or retracted in the protective guard. The protective guard is spring biased to a guarded position which covers the hypodermic needle. A ratcheting mechanism provided on the protective guard and the syringe barrel restricts that movement of the protective guard which exposes the hypodermic needle. When the needle has been used and is being removed from the patient's body, the syringe barrel and hypodermic needle retract inside the protective guard and the ratcheting mechanism may be disabled to permanently secure the needle in the guarded position.

14 Claims, 4 Drawing Sheets

HYPODERMIC SYRINGE

BACKGROUND OF THE INVENTION

1. Field of the Invention

This invention relates to a hypodermic syringe and more particularly to a hypodermic syringe having a protective device to prevent users of the syringe from being inadvertently scratched or cut by contaminated needles.

2. Description of the Prior Art

Health care personnel are frequently encountering the hazard of being pricked or otherwise inadvertently scratched or cut by contaminated hypodermic needles. The health care personnel are at risk in both blood drawing and medicine injection procedures. The patient from whom the blood is drawn or medicine is administered may have infectious agents, such as the hepatitis virus or the human immunodeficiency virus, in his blood. If so, accidental contact between the contaminated needle and the health care personnel may transmit diseases such as hepatitis or AIDS from the patient to the health care worker.

Various devices have been proposed for use, or otherwise used, in the past to cover the needle portion of a hypodermic syringe. Some of these devices leave the needle exposed for a short time after removal from the patient. After this short time, a protective cover is extended over the needle to prevent inadvertent contact therewith. However, such devices do not eliminate the risk that the health care personnel can be struck by the needle immediately upon removal from the patient. Consequently, such prior art devices do not prevent the potentially hazardous, inadvertent contact with the needle of the hypodermic syringe.

Other devices which have been proposed for use do prevent contact with the contaminated hypodermic needle upon removal from the patient, but are very clumsy and awkward to use. One example of such a device is a hypodermic syringe having a spring-loaded covering sheath in which the needle is maintained in a retracted position. The sheath is first provided along the patient's body and the hypodermic syringe is extended through the sheath in such a manner that the needle is inserted into the patient. Upon removal of the needle from the patient, the hypodermic syringe is again retracted into the sheath and the sheath is removed from contact with the patient's body. Such a device is awkward to use because the initial contact between the device and the patient is the cover sheath and not the needle of the hypodermic syringe. Such a device prevents the health care personnel from getting a true "feel" of the area in which the needle is to be inserted. Such a "feel" is especially necessary when the procedure being performed by the health care personnel is the drawing of blood and the location of the needle insertion is of prime importance.

Other safety devices which are adapted to cover the needle immediately upon removal from the patient are difficult to operate and require the use of two hands. Typical of such devices are frictionally sliding cover sheaths on hypodermic syringes and sheaths which are secured to the syringe by threads and require that the sheath be rotated relative to the hypodermic body. Such devices require the use of both hands of the health care personnel, thereby preventing the health care personnel from attending to the patient with his or her spare hand. Moreover, such devices do not cover the needle in the event that the syringe is accidentally dropped. There remains a need for a syringe device which eliminates exposure of an operator to a contaminated needle but affords the operator the freedom of using his or her spare hand to attend to the patient.

SUMMARY OF THE INVENTION

The invention is a device for preventing the inadvertent exposure of a contaminated needle of a hypodermic syringe to a health care personnel. The device includes a syringe barrel having a barrel flange provided at one end and a hypodermic needle provided at the other end. A plunger is provided at the end opposite the hypodermic needle. A protective guard adapted to fit around the syringe barrel is also provided. The protective guard is adapted to move axially along the syringe barrel between a first position which covers the hypodermic needle and a second position which exposes the hypodermic needle. Spring means are provided inside the protective guard between the external needle end of the syringe barrel and the internal needle end of the protective guard to force the syringe barrel and needle into the protective guard and maintain the protective guard in the first position. In use, the protective guard is axially moved to the second position to enable the needle to be inserted into a patient. When the needle is being removed from the patient or when the syringe is accidentally dropped, the spring moves the protective guard to the first position.

Locking means are provided on both the syringe barrel and the protective guard for securing the protective guard in the first position after the needle has been removed from the patient. The locking means preferably includes serrations provided on one side of the syringe barrel. A ratcheting mechanism is provided on the protective guard to engage the serrations and prevent relative movement of the protective guard and the syringe barrel. Engagement of a release trigger connected to the ratcheting mechanism removes the ratcheting mechanism from the serrations provided on the syringe barrel. Preferably, the release member is provided adjacent the guard flange of the protective guard so that the health care personnel can, with one hand, grasp the hypodermic syringe, depress the plunger of the syringe and depress the release trigger of the protective guard.

DESCRIPTION OF THE PREFERRED EMBODIMENTS

Figure 1:
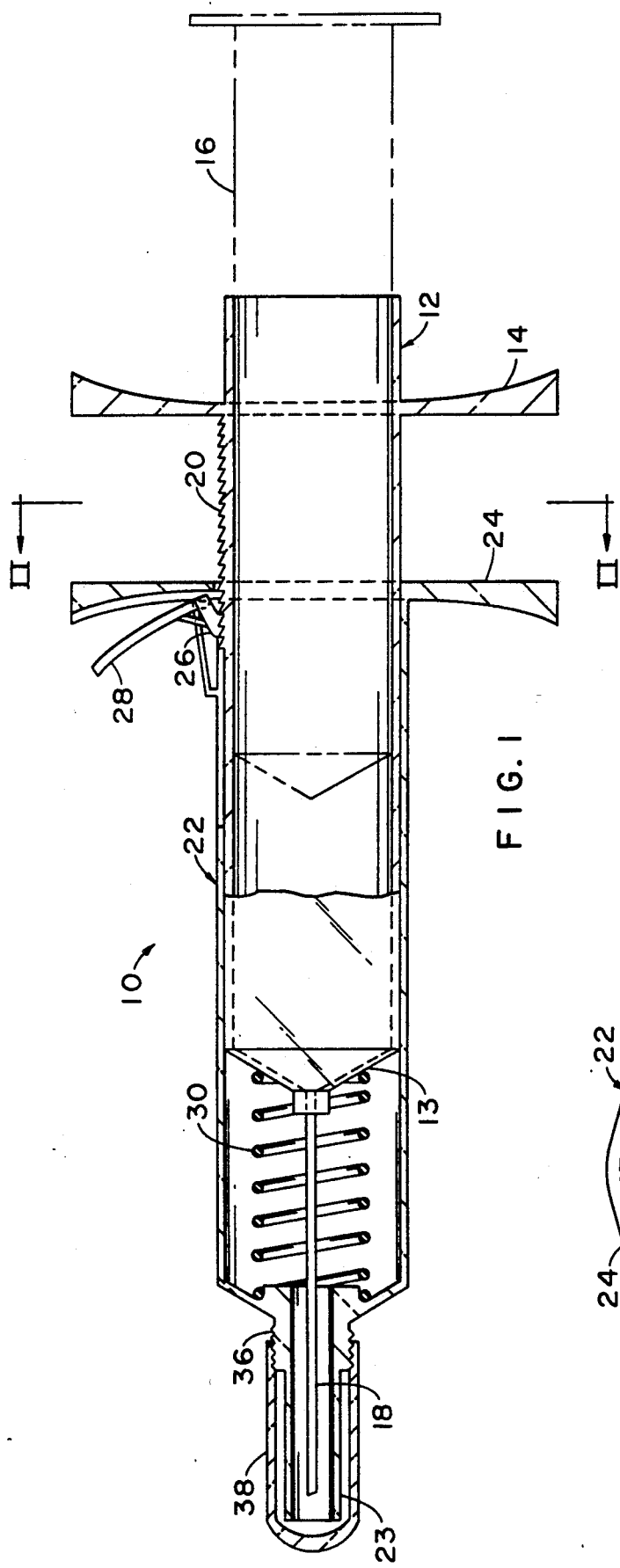
FIG. 1 is a diagrammatic representation of a side view of a presently preferred embodiment of the hypodermic needle protection device of the present invention.
Figure 2:
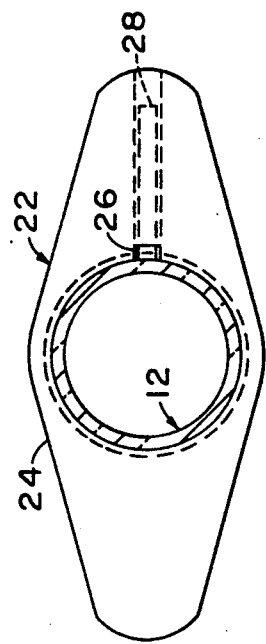
FIG. 2 is a top view of the hypodermic needle protection device of FIG. 1 taken on line II—II without the plunger.

As shown in FIG. 1, safety syringe device 10 includes syringe barrel 12 having barrel flange 14 at the proximal end and hypodermic needle 18 at the distal end 13. Generally, the distance of barrel flange 14, as measured from the proximal end of barrel 12, is inversely proportional to the capacity of syringe barrel 12. As the capacity of syringe barrel 12 becomes larger, the length of barrel flange 14 from the proximal end of the barrel 12 becomes smaller. Plunger 16 provided at the proximal end is adapted to be depressed into syringe barrel 12 to expel fluid out needle 18. Serrations 20 are provided along a side portion of the syringe barrel 12 near barrel flange 14. Serrations 20 are sized and positioned to restrict axial movement of protective guard 22 in a direction that exposes needle 18. Serrations 20 do not restrict axial movement of protective guard in a direction that will cover needle 18.

Protective guard 22 is sized to fit over the syringe barrel 12 and hypodermic needle 18. Preferably, end 23 of protective guard 22 may be formed or sized to fit over a medicine vial. Protective guard 22 includes guard flange 24 which is sized to correspond to barrel flange 14 of syringe barrel 12. When guard flange 24 is brought into contact with barrel flange 14, needle 18 is exposed. Spring 30 is provided inside protective guard 22. Spring 30 engages the distal interior end portion of protective guard 22 and the external distal portion of syringe barrel 12. Spring 30 provides a continuous force on syringe barrel 12 which causes the syringe barrel 12, including hypodermic needle 18, to be retracted into protective guard 22.

Ratcheting member 26 of protective guard 22 is adapted to engage serrations 20 on syringe barrel 12 and secure syringe barrel 12 in a retracted position relative to protective guard 22. A release trigger 28 is operatively connected to ratcheting member 26. When release trigger 28 is depressed into guard flange 24, ratcheting member 26 is removed from serrations 20, thereby allowing relative movement of protective guard 22 with respect to syringe barrel 12 to expose needle 18. As long as ratcheting member 26 is engaged with serrations 20, syringe barrel 12 cannot be forced into a position which exposes needle 18. Once ratcheting member 26 is disengaged from serrations 20, the user of syringe 10 is able to move protective guard 22 to expose needle 18.

Figure 6:
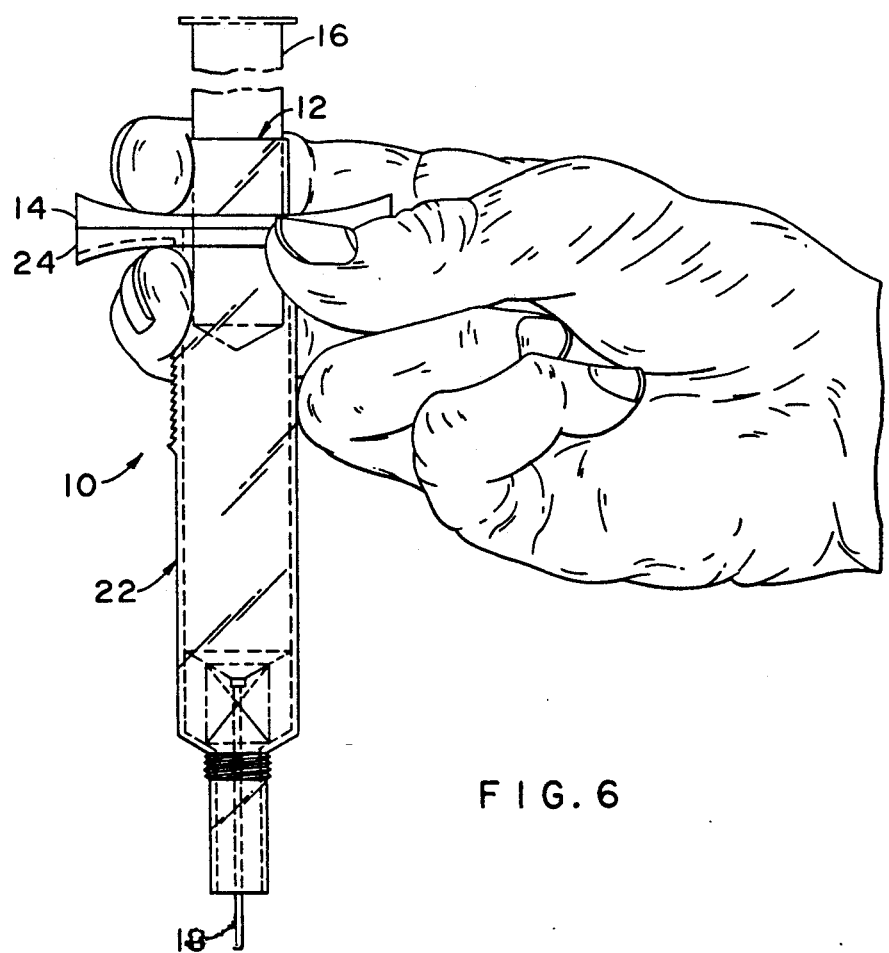
FIG. 6 is a diagrammatic representation of the hypodermic needle protection device of the present invention shown in use in a human hand.

Preferably, release trigger 28 is operated by pushing trigger 28 towards guard flange 24. This manner of operation permits the user of the safety syringe device 10 to depress the plunger 16 with the thumb of one hand and depress the release trigger 28 with the index finger of the same hand. For expeditious use, syringe 10 can be grasped and operated by health care personnel using only the fore finger, middle finger and thumb on one hand as shown in FIG. 6. Preferably, guard flange 24 and barrel flange 14 include an arched surface to assist in grasping and securely holding the syringe 10.

In order to provide smooth axial movement of protective guard 22 relative to syringe barrel 12, an axial guiding groove (not shown) may be provided along protective guard 22. A guiding lug provided along the side of syringe barrel 12 is engaged within the axial guiding groove. The cooperation of the guiding lug and guiding groove maintains the axial movement of protective guard 22 relative to syringe barrel 12. The guiding lug may also provide a positive stop to prevent further retraction of syringe barrel 12 within protective guard 22 after ratcheting mechanism 26 is disengaged from serrations 20. Alternatively, serrations 20 may also serve as the guideway for axial movement. In such event, a guard extension stop 32, shown in FIGS. 3-5, may be provided on protective guard 22 to limit retraction of syringe barrel 12 within protective guard 22. Guard extension stop 32 is sized and positioned to engage barrel stop means 34 provided on syringe barrel 12 and prevent further axial movement of protective guard 22 relative to syringe barrel 12.

Figure 3:
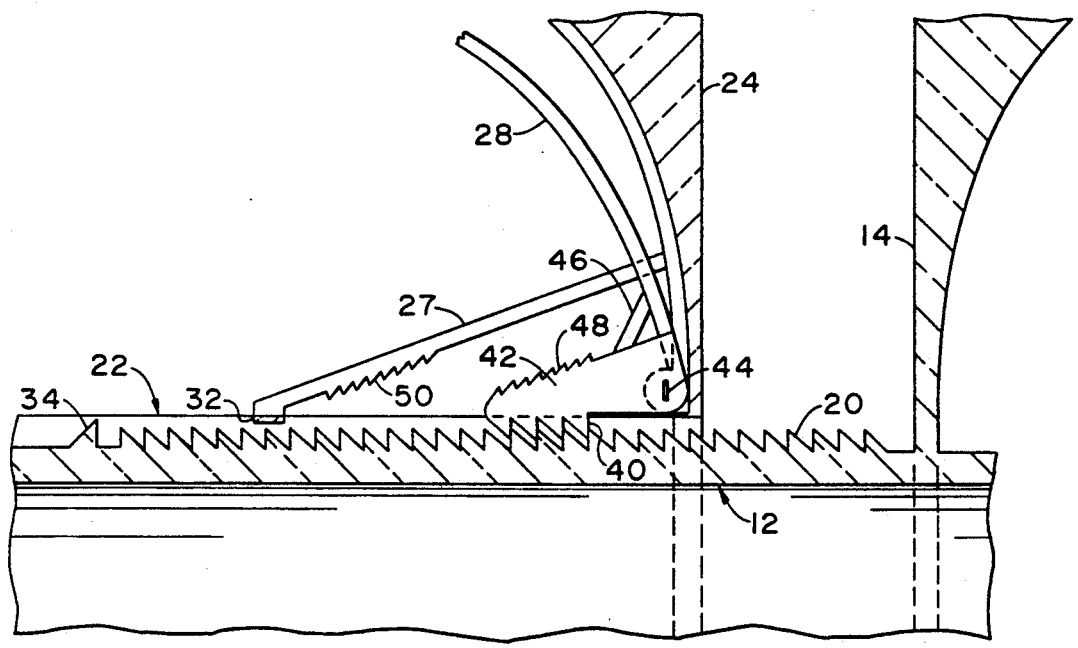
FIG. 3 is a diagrammatic representation of a sectional side view of a first presently preferred embodiment of the locking means for use with the protection device of FIG. 1.
Figure 4:
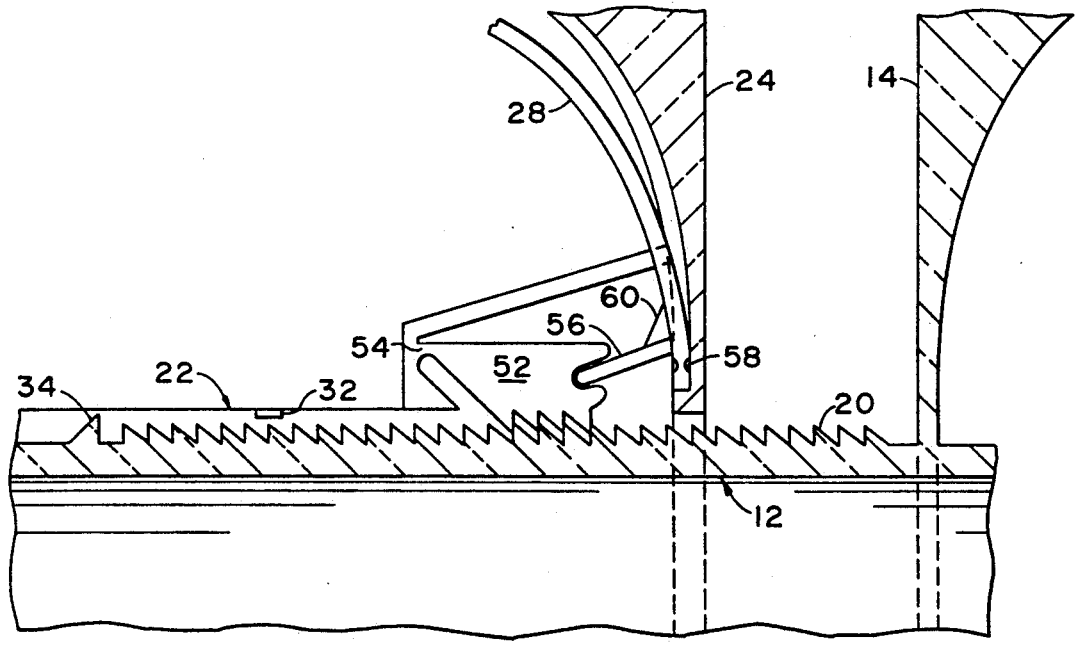
FIG. 4 is a diagrammatic representation of a side sectional view of a second presently preferred embodiment of the locking means for use with the protection device of FIG. 1.
Figure 5:
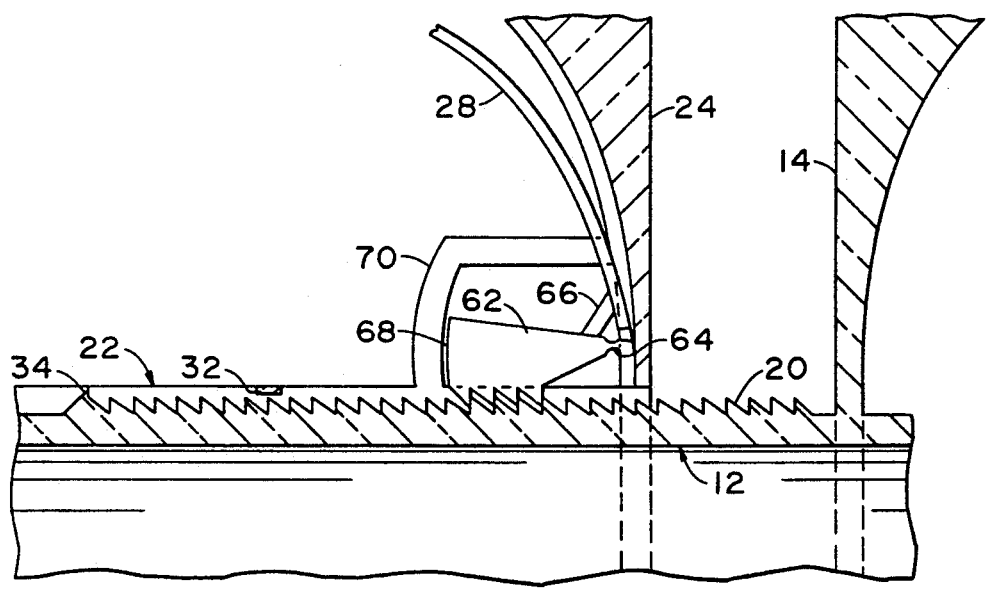
FIG. 5 is a diagrammatic representation of a side sectional view of a third presently preferred embodiment of the locking means for use with the protection device of FIG. 1.

FIGS. 3, 4 and 5 show three alternative embodiments of the ratcheting mechanism 26 which can be used in the present invention. In the ratcheting mechanism 26 of FIG. 3, trigger 28 is connected to pawl 42 by means of shear web 46. Pawl 42 is provided with serrations 40 which correspond to serrations 20 provided on syringe barrel 12. As trigger 28 is pushed towards guard flange 24, pawl 42 pivots about pawl hinge 44 and is lifted away from serrations 20. Once pawl 42 has been disengaged from serrations 20, protective guard 22 is free to move axially relative to syringe barrel 12 to expose needle 18. Shear web 46 connects trigger 28 to pawl 42. Shear web 46 is formed from a very thin, brittle material which can sustain a pulling force but collapses under a compressive force. Once syringe barrel 12 has been permanently withdrawn within protective guard 22, trigger 28 may be disabled by bending it away from guard flange 24. Such bending breaks shear web 46, thereby disconnecting pawl 42 from trigger 28.

FIG. 3 also shows a secondary locking mechanism to secure needle 18 in a retracted position. Serrations 48 provided on the upper side of pawl 42 correspond to serrations 50 provided on the inner surface of ratcheting mechanism housing 27. In the event that pawl 42 breaks free of guard 22, serrations 50 on housing 27 engage serrations 48 on pawl 42. Because pawl 42 is rendered immobile relative to barrel 12 by the engagement of serrations 20 and 40, the engagement of serrations 48 and 50 renders guard 22 immobile relative to barrel 12.

FIG. 4 shows an alternative ratcheting mechanism 26 in which trigger 28 disengages pawl 52 from serrations 20 by means of pawl lever 56. Pawl lever 56 is connected to trigger 28 at solid trigger hinge 58. Pawl 52 which is provided with serrations that correspond to serrations 20 provided on syringe barrel 12 pivots about pawl hinge 54 which is provided opposite pawl lever 56. Pawl lever 56 is attached to trigger 28 by means of shear web 60. The operation of the trigger 28 to release pawl 52 from the serrations 20 provided on syringe barrel 12 is the same as for the embodiment shown in FIG. 3. Once syringe barrel 12 has been permanently withdrawn within protective guard 22, trigger 28 may be disabled by bending it forward, thereby breaking shear web 60 and disconnecting pawl lever 56 from trigger 28. Such breaking prevents trigger 28 from further acting indirectly on pawl 52 to release pawl 52 from serrations 20.

A third embodiment for the ratcheting mechanism 26 is shown in FIG. 5. Therein, trigger 28 is connected to pawl 62 by means of shear web 66. As trigger 28 is pulled toward guard flange 24, pawl 62 which is provided with serrations that correspond to serrations 20 provided on syringe barrel 12 pivots about pawl hinge 64 and is released from engagement with serrations 20. Pawl face 68 is shaped to correspond to the housing 70 containing the locking means. Once syringe barrel 12 has been permanently withdrawn within protective guard 22, trigger 28 may be bent away from guard flange 24 to break shear web 66. The breaking of shear web 66 disables trigger 28.

Preferably, all components of ratcheting mechanism 26 are formed from a resilient plastic. The use of a resilient plastic ensures that pawl 42, 52, 62 is pushed back into engagement with serrations 20. However, shear web 46, 60, 66 may be formed from a very thin brittle plastic that breaks upon compression. The use of such a brittle plastic permits trigger 28 to be disabled by bending trigger 28 away from barrel flange 14, thus securing syringe barrel 12 in a permanently retracted position within protective guard 22.

Typical hypodermic syringes are provided with cap threads on the syringe body adjacent the hypodermic needle. These cap threads are adapted to receive a cap which covers over the hypodermic needle to maintain sterility of the needle and prevent the health care personnel from being pricked or otherwise struck by the needle prior to use on a patient. In the present invention, identical cap threads 36 are provided on protective guard 22. Such cap threads 36 are adapted to receive cover cap 38 for the hypodermic syringe. As an added feature, the end of cap 38 may be provided with increased thickness to prevent needle 18 from accidentally penetrating cap 38.

Figure 7:
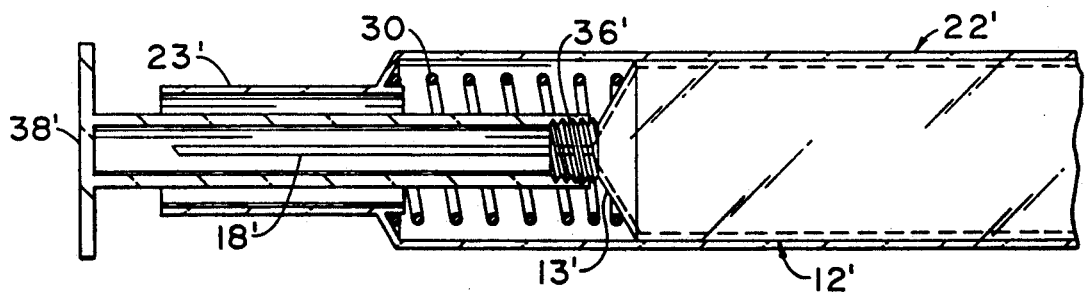
FIG. 7 is a diagrammatic representation of a side view of the distal portion of the hypodermic needle protection device of FIG. 1 showing an alternative cap design.

FIG. 7 shows an alternative design for the cap assembly. In the alternative design, cap threads 36' are provided on the extreme distal portion 13' of syringe barrel 12'. Such cap threads are adapted to receive elongated cover cap 38'. Cover cap 38' is sized to fit between hypodermic needle 18' and the wall of extreme distal portion 23' of protective guard 22'. The cap design of FIG. 7 maintains the sterility of hypodermic needle 18' independent of the sterility of protective guard 22'.

While we have described a present preferred embodiment of the invention, it is to be distinctly understood that the invention is not limited thereto but may be otherwise embodied and practiced within the scope of the following claims.

We claim:

1. A device for preventing exposure of a contaminated hypodermic needle comprising:
    a syringe barrel having a flange provided at a proximal end and a hypodermic needle provided at a distal end, said proximal end adapted to receive a plunger;
    a protective guard adapted to fit around said syringe barrel, said protective guard adapted to move between a first position covering said hypodermic needle and a second position exposing said hypodermic needle;
    means for moving said protective guard from said first position to said second position;
    spring means provided inside said protective guard and extending from an interior proximal end of said protective guard to an exterior proximal end of said syringe barrel, said spring means providing a force on said syringe barrel to retract said syringe barrel within said protective guard, said spring means adapted to retract said syringe barrel within said protective guard automatically when released; and
    locking means provided on said syringe barrel and said protective guard to restrict axial movement of said protective guard toward said second position, said locking means comprising a serrated portion provided on said syringe barrel and ratcheting means provided on said protective guard, said ratcheting means adapted to engage said serrated portion.

2. The device of claim 1 further comprising means for disabling said means for moving said protective guard.

3. The device of claim 1 further comprising a release trigger operatively connected to said ratcheting means, said release trigger adapted to disengage said ratcheting means from said serrated portion, thereby allowing axial movement of said protective guard toward said second position.

4. The device of claim 1 further comprising cap means, said cap means adapted to cover said needle and maintain sterility of said needle.

5. The device of claim 4 wherein said cap means comprises a threaded cap member adapted to cover said hypodermic needle and threads provided on said protective guard, said threads adapted to receive said cap member.

6. The device of claim 4 wherein said cap means comprises a threaded cap member adapted to cover said hypodermic needle and threads provided on said syringe body, said cap member adapted to be inserted within said protective guard.

7. The device of claim 1 wherein said protective guard comprises a guard flange, said guard flange adapted to engage said syringe barrel flange when said protective guard is moved to said second position to expose said needle.

8. The device of claim 7 wherein said guard flange and said barrel flange comprise at least one arched surface.

9. The device of claim 1 wherein the distance of said syringe barrel flange from the proximal end of said barrel is inversely proportional to the capacity of said syringe barrel.

10. A device for preventing exposure of a contaminated hypodermic needle comprising:
    a syringe barrel having a flange provided at a proximal end and a hypodermic needle provided at a distal end, said proximal end adapted to receive a plunger;
    a protective guard adapted to fit around said syringe barrel, said protective guard adapted to move between a first position covering said hypodermic needle and a second position exposing said hypodermic needle;
    means for moving said protective guard from said first position to said second position;
    spring means provided inside said protective guard and extending from an interior proximal end of said protective guard to an exterior proximal end of said syringe barrel, said spring means providing a force on said syringe barrel to retract said syringe barrel within said protective guard;
    locking means provided on said syringe barrel and said protective guard to restrict axial movement of said protective guard toward said second position, wherein said locking means includes a serrated portion provided on said syringe barrel and a ratcheting means provided on said protective guard, said ratcheting means adapted to engage said serrated portion, wherein said ratcheting means comprises a pawl having serrations which correspond to said serrated portion, said pawl connected to said trigger by means of a shear web; and a release trigger operatively connected to said ratcheting means, said release trigger adapted to disengage said ratcheting means from said serrated portion, thereby allowing axial movement of said protective guard toward said second position.

11. The device of claim 10 further comprising a housing provided on said protective guard, said housing covering said ratcheting means, wherein an inner surface of said housing and an outer surface of said pawl are each provided with serrations, said serrations on said pawl adapted to engage said serrations on said housing in the event said pawl breaks off from said trigger.

12. The device of claim 10 wherein said trigger is disabled by bending said trigger away from said barrel flange to break said shear web.

13. The device of claim 12 wherein said pawl pivots about a hinge provided on said trigger.

14. The device of claim 12 further comprising a lever connected to said trigger wherein said pawl pivots about a hinge provided opposite said lever.

* * * * *